(12) United States Patent
Kates et al.

(10) Patent No.: US 6,792,114 B1
(45) Date of Patent: Sep. 14, 2004

(54) INTEGRATED HEARING AID PERFORMANCE MEASUREMENT AND INITIALIZATION SYSTEM

(75) Inventors: James Mitchell Kates, Niwot, CO (US); John Laurence Melanson, Boulder, CO (US); Eric Lindemann, Boulder, CO (US)

(73) Assignee: GN ReSound A/S, Denmark (DE)

( * ) Notice: Subject to any disclaimer, the term of this patent is extended or adjusted under 35 U.S.C. 154(b) by 0 days.

(21) Appl. No.: 09/413,732

(22) Filed: Oct. 6, 1999

Related U.S. Application Data
(60) Provisional application No. 60/103,166, filed on Oct. 6, 1998.

(51) Int. Cl.$^7$ .......................... H04R 29/00; H04R 27/00
(52) U.S. Cl. ............................................ 381/60; 381/83
(58) Field of Search ..................... 381/60, 83; 600/559; 73/585

(56) References Cited

U.S. PATENT DOCUMENTS

| | | | | |
|---|---|---|---|---|
| 5,999,631 | A | * 12/1999 | Porayath et al. | ............... 381/93 |
| 6,366,863 | B1 | * 4/2002 | Bye et al. | ...................... 702/57 |

OTHER PUBLICATIONS

PCT Application No. PCT/US99/06682, entitled, "Feedback Cancellation Improvements," Nov. 25, 1999 as International Publication No. WO 99/60822.
PCT Application No. PCT/US99/06642, entitled, "Apparatus and Methods for Combining Audio Compression and Feedback Cancellation in a Hearing Aid," published Oct. 7, 1999 as International Publication No. WO 99/51059.
Revit, Lawrence J. "Using Coupler Tests in the Fitting of Hearing Aids," *Strategies for Selecting and Verifying Hearing Aid Fittings*, Ed. Michael Valente, pp. 64–87.
Schweitzer, Christopher. "Development of Digital Hearing Aids," Trends in Amplification 2(2), New York: Woodland, 1997, pp. 40–77.
Sanborn, Eric. "Predicting Hearing Aid Response in Real Ears," J. Acoust. Soc. Am. 103(6), Jun. 1998, pp. 3407–3417.
Egolf, David P., Henry C. Howell, Kim A. Weaver, and D. Steven Barker. "The Hearing Aid Feedback Path: Mathematical Simulations and Experimental Verification," J. Acoust. Soc. Am. 78(5), Nov. 1985, pp. 1578–1587.
Bade, Priscilla F., A. Maynard Engebretson, Arnold F. Heidbreder, and Arthur F. Niemoeller. "Use of a Personal Computer to Model the Electroacoustics of Hearing Aids," J. Acoust. Soc. Am. 75(2), Feb. 1984, pp. 617–620.
Egolf, David P. "Mathematical Predictions of Electroacoustic Frequency Response of *In Situ* Hearing Aids," J. Acoust. Soc. Am. 63(1), Jan. 1978, pp. 264–271.

* cited by examiner

*Primary Examiner*—F. W. Isen
*Assistant Examiner*—Elizabeth McChesney
(74) *Attorney, Agent, or Firm*—Jennifer L. Bales; Macheledt Bales & Heidmiller LLP

(57) ABSTRACT

A digital hearing aid according to the present invention is capable of measuring its own performance. The hearing aid includes a test signal generator for feeding a test signal into the hearing aid amplifier. The response to the test signal is acquired at a specific point in the hearing aid, depending upon what aspect of performance is to be measured. Various elements of the hearing aid and/or the hearing aid feedback may be bypassed. The hearing aid further includes the capability of initializing hearing aid parameters based upon the performance measurements. The measurement and initialization capability may be entirely integral to the hearing aid, or an external processor may be used to download the measurement program and the run time program, and assist in computing the parameters.

19 Claims, 5 Drawing Sheets

US 6,792,114 B1

INTEGRATED HEARING AID PERFORMANCE MEASUREMENT AND INITIALIZATION SYSTEM

This application claims the benefit of U.S. Provisional Application No. 60/103,166, filed Oct. 6, 1998.

BACKGROUND OF THE INVENTION

Pending patent application Ser. No. 09/081,474, filed May 19, 1998 and entitled "Feedback Cancellation Improvements" is incorporated herein by reference.

1. Field of the Invention

The present invention relates to apparatus and methods for integrated hearing aid performance measurement and initialization.

2. Description of the Prior Art

In general, hearing aid performance measurements, whether on the production line or in the individual wearer's ear, have used an external test system that generates the test signal and analyzes the response. The measurement of the frequency response of a hearing aid in the ear, for example, typically requires the use of external signal generating and measurement equipment (Egolf, D. P., Tree, D. R., and Feth, L. L., 1978, "Mathematical predictions of electroacoustic frequency response of in situ hearing aids", J. Acoust. Soc. Am., Vol. 63, pp 264–271; Bade, P. F., Engebretson, A. M., Heidbreder, A. F., and Niemoeller, A. F., 1984, "Use of personal computer to model the electroacoustics of hearing aids", J. Acoust. Soc. Am., Vol. 75, pp 617–620; Sanborn, P-E, 1998, "Predicting hearing aid response in real ears", J. Acoust. Soc. Am., Vol. 103, pp 3407–3417). Measurements of the feedback path from the receiver back to the hearing aid microphone also have required the use of external equipment (Egolf, D. P., Howell, H. C., Weaver, K. A., and Barker, S., 1985, "The hearing aid feedback path: Mathematical simulations and experimental verification", J. Acoust. Soc. Am., Vol. 78, pp 1578–1587), as does the determination of the maximum output signal level (Revit, L. J., 1994, "Using coupler tests in the fitting of hearing aids", in Strategies for Selecting and *Verifying Hearing Aid Fittings*, ed. by M. Valente, New York: Thieme Medical Publishers).

A conventional digital hearing aid is shown in FIG. 1A (prior art). Input sound signal 152 is converted into an audio signal by microphone 154. Hearing aid processor 156 is a digital signal processor (analog to digital conversion at the input and digital to analog conversion at the output are omitted for clarity). The processed audio signal is amplified by amplifier 158 and converted back into a sound signal 162 by receiver 160. Conventional digital hearing aids like hearing aid 110 use digital signal processing for the run time system, but still rely on conventional measurement equipment for measuring the hearing aid response and setting the processing parameters. Most digital hearing aids do not contain a programmable DSP circuit, but instead use a dedicated processor that can only perform the run time processing operations (Schweitzer, C., "Development of digital hearing aids", Trends in Amplification, Vol 2, pp 41–77). These hearing aids are therefore incapable of performing any measurements, calibration, or parameter initialization.

An example of a conventional hearing aid test system 100 is illustrated in FIG. 1B (prior art). The hearing aid 110 to be evaluated is placed in a test box 102. The input to hearing aid 110 is an acoustic test signal 109 from loudspeaker 108, also contained in test box 102. Hearing aid 102 is configured to perform the desired signal processing function, such as linear gain or multiband compression. The hearing aid output is an acoustic signal that is then piped to acoustic coupler 114 via a piece of tubing 113. The acoustic coupler consists of a microphone 118 placed at the end of a cavity 116. An external computer 104 controls the generation of test signal 109 and acquires and processes the microphone response 120. Display 116 displays test results. A commercial hearing aid test system that conforms to this basic design is the Fonix 6500, manufactured by Frye Electronics, Inc, Tigard, Oreg. 97223.

For independently performing measurements, the digital hearing aid must be able to accept a program for generating a test signal and recording the response as well as accept the program for the run time processing. A need remains in the art for apparatus and methods to enable a hearing aid to measure its own performance characteristics and to use those measurements to set its processing parameters.

SUMMARY OF THE INVENTION

It is an object of the present invention to provide apparatus and methods to enable a hearing aid to measure its own performance characteristics and to use those measurements to set its processing parameters.

In addition to providing digital processing of the audio signal being amplified to compensate for the hearing loss, the programmable DSP circuit of a hearing aid according to the present invention is also used to measure the characteristics of the hearing aid on the production line or fitted to the individual ear. Such a hearing aid might perform measurements such as maximum output signal level, distortion, or the response characteristics of the microphone or receiver. By using the signal processing system described herein, these and other tests can be performed all or in part by the hearing aid under test. A test program is loaded into the hearing aid and the tests are performed. Then the program used for the run time amplification, along with any processing parameters set during the tests, is loaded into the hearing aid memory.

DETAILED DESCRIPTION OF THE PREFERRED EMBODIMENT

A digital hearing aid according to the present invention is used to measure several aspects of the hearing aid system. The transfer function of the feedback path, consisting of the amplifier, receiver, feedback acoustics, and microphone in series, can be measured in the ear using the hearing aid microphone. The transfer function of the series combination of the amplifier and receiver, and the maximum output levels and distortion for the amplifier receiver combination, can be measured as well using an external microphone. Once the receiver characteristics are known, the hearing aid microphone transfer function can also be determined. These measurements are possible because the hearing aid contains a digital signal processing (DSP) integrated circuit that provides a programmable computer inside the hearing aid.

Figure 1A:
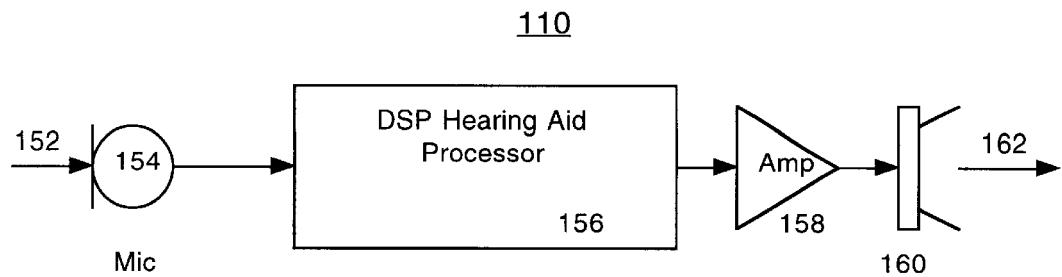
FIG. 1A (prior art) shows a conventional hearing aid.
Figure 1B:
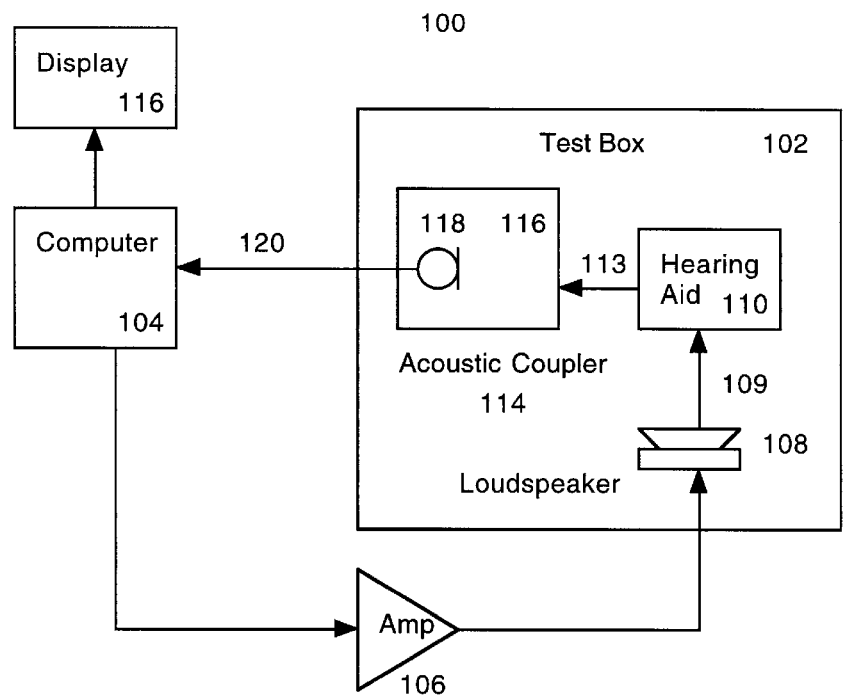
FIG. 1B (prior art) shows a conventional hearing aid test system.
Figure 2:
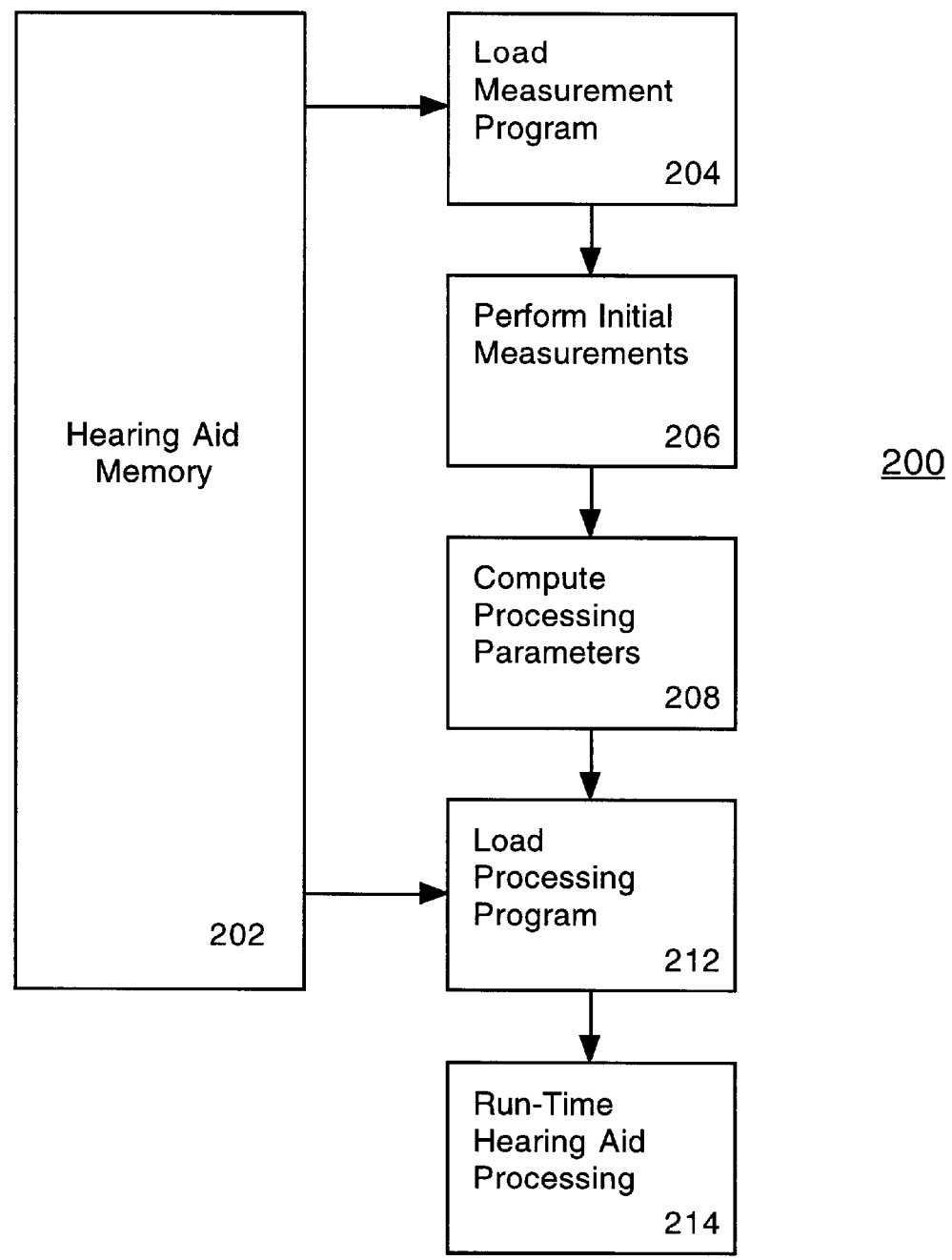
FIG. 2 is a flow diagram showing a first integrated hearing aid performance measurement and initialization method according to the present invention.

FIG. 2 is a flow diagram showing a first integrated hearing aid performance measurement and initialization method 200. The hearing aid might be very similar to that shown in FIG. 1A, but the hearing aid processor is a programmable DSP. The initial processing steps 204–208 shown in FIG. 2 are preferably run prior to the run time operation 214 of the hearing aid, as an initialization process. This initialization may be performed once, or each time the hearing aid is turned on. In FIG. 2, the initialization process is entirely integrated within the hearing aid. The code used to perform measurements and set initialization parameters is resident in hearing aid memory 202, and all processing is performed within the hearing aid.

Figure 4:
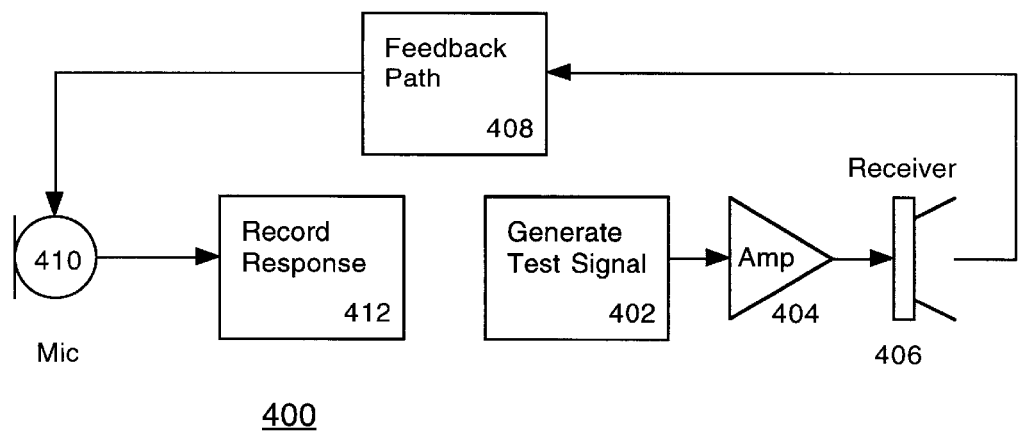
FIG. 4 is a block diagram showing a first configuration for performing the measurement steps of FIGS. 3 and 4.
Figure 5:
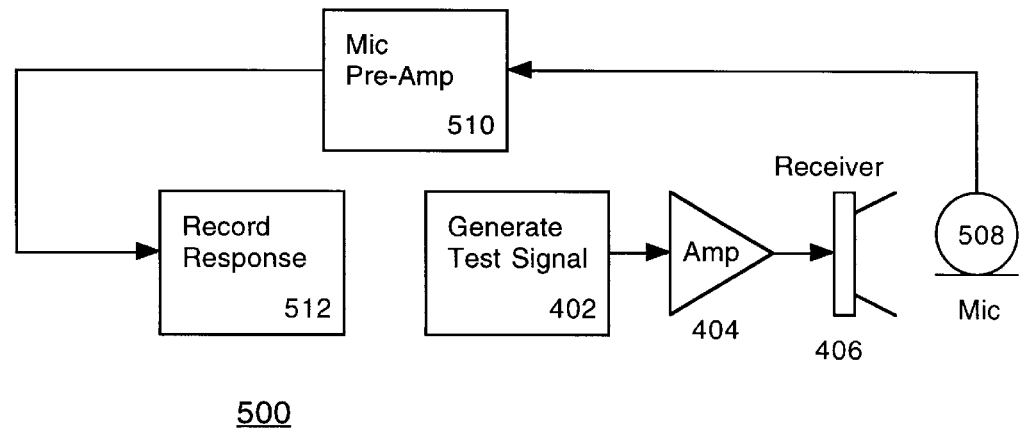
FIG. 5 is a block diagram showing a second configuration for performing the measurement steps of FIGS. 3 and 4.
Figure 6:
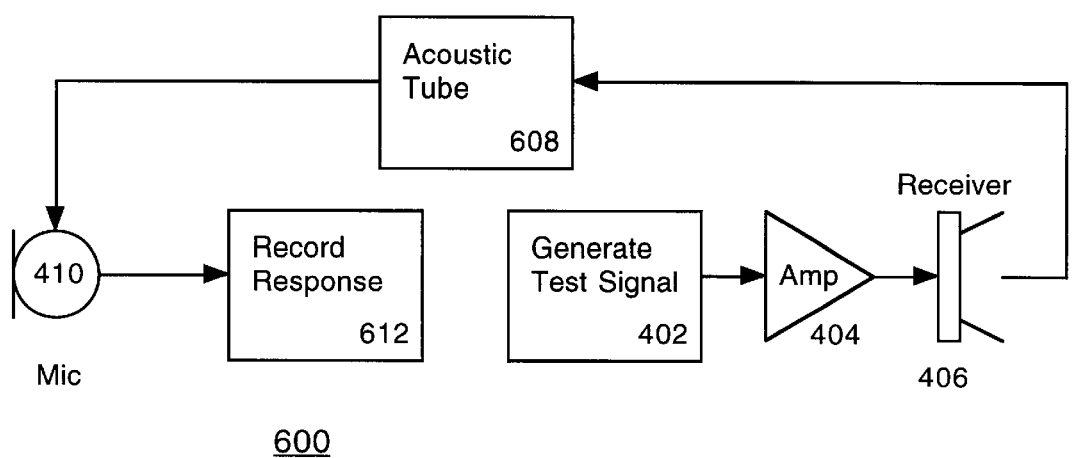
FIG. 6 is a block diagram showing a third configuration for performing the measurement steps of FIGS. 3 and 4.

In step 204, the measurement program is loaded from hearing aid memory 202. Preferably, this program is stored in some form of rewritable memory, so the program can be updated if desired. Step 206 performs measurements of hearing aid performance, for example transfer functions of various combinations of hearing aid elements. FIGS. 4–6 illustrate various measurement configurations which could be employed. In step 208, processing parameters are computed from these measurements. In step 212, the hearing aid run time program is loaded into operating memory, and in step 214, run time hearing aid processing begins.

Note that the two step procedure of loading the initialization code followed by loading the run time code is most appropriate when the hearing aid has a limited amount of program memory; if enough memory is available, the initialization and run time code can be combined into a single program.

Figure 3:
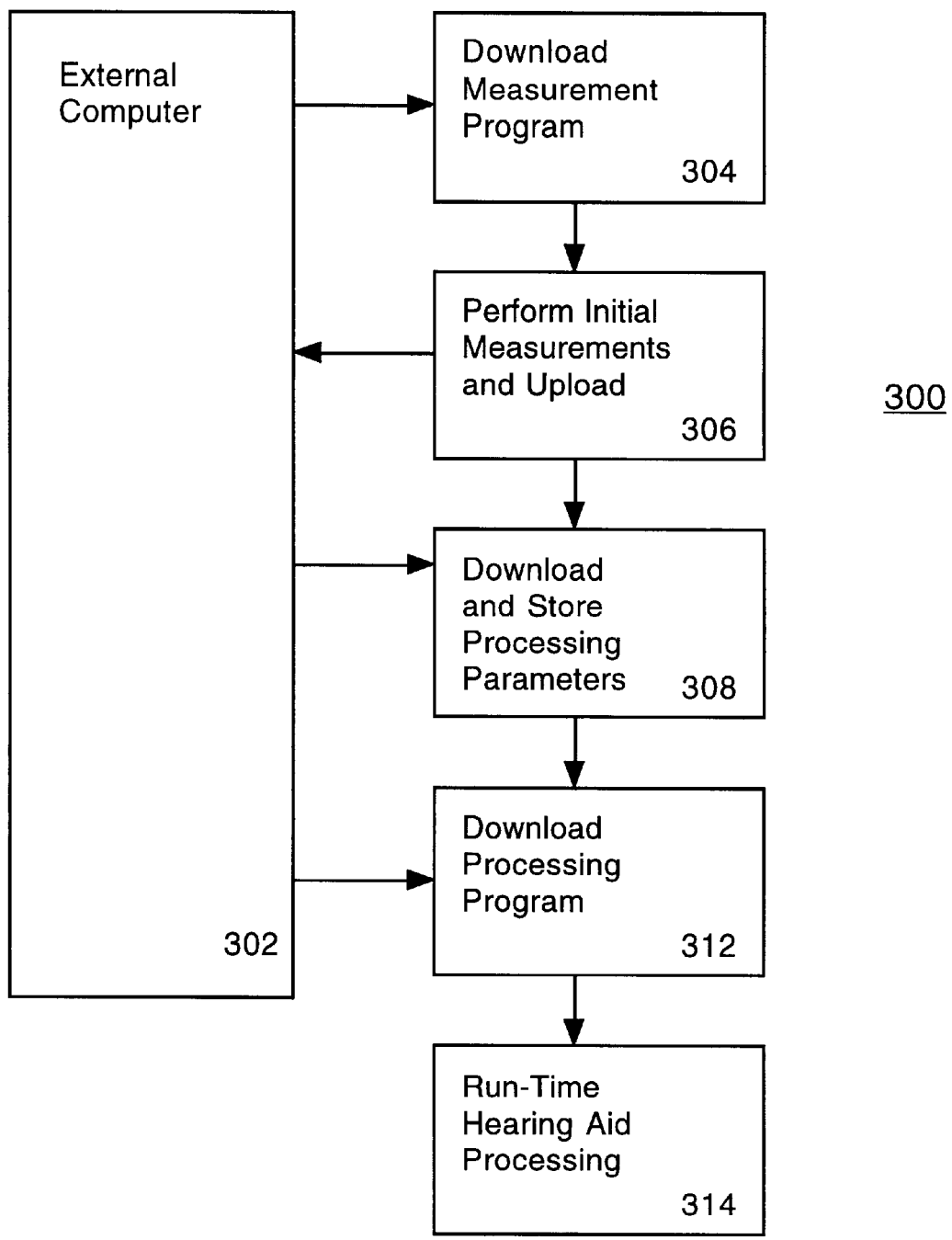
FIG. 3 is a flow diagram showing a second partially integrated hearing aid performance measurement and initialization method according to the present invention.

FIG. 3 is a flow diagram showing a second, partially integrated, hearing aid performance measurement and initialization method. In this embodiment, the hearing aid interacts with a host computer 302 to download program code and process the measurements. In step 304 the measurement program is downloaded from host computer 302. The hearing aid DSP runs the program and acquires data in step 306, and may also partially process the data. The raw or partially processed data is then sent up to host computer 302, which computes the processing parameters. Step 308 stores the processing parameters for use by the run time processing program. The run time code is then downloaded to the hearing aid in step 312. Real time processing begins in step 314.

The method shown in FIG. 3 might be used when there is simply not enough storage memory in the hearing aid for both the measurement program and the run time program. Thus, each must be separately loaded into the hearing aid when needed. In general, the initialization is performed only once in the scenario shown in FIG. 3, since an external computer is required to load the two programs. However, if better initialization or run time programs became available, the process of FIG. 3 could be repeated.

FIGS. 4–6 show configurations for performing measurement steps 206 and 306 of FIGS. 2 and 3. FIG. 4 is a block diagram showing a first measurement configuration. The characteristics of the feedback path, which includes the amplifier 404, receiver 406, and microphone 410 along with the acoustic and mechanical feedback 408, can be measured by exciting the system with a probe signal 402 and recording the response 412 at the hearing aid microphone 410.

The impulse response of the feedback path can be obtained, for example, by using a periodic maximal-length sequence as the probe and accumulating the corresponding periods of the microphone response. The circular correlation of the microphone response with one period of the excitation will then give the impulse response of the feedback path. System identification techniques can then be used to produce an all-zero, all-pole, or pole-zero model of the feedback path from the impulse response. An alternative would be to excite the system with a white noise probe sequence and adapt a set of filter coefficients to produce the model of the feedback path.

FIG. 5 is a block diagram showing a second configuration for performing measurement steps 206 and 306 of FIGS. 2 and 3. The characteristics of receiver 406 can be determined using the configuration of FIG. 5. As in the case of the FIG. 4 configuration, a test signal is generated by block 402 which passes through amplifier 404 and receiver 406. However, in this configuration, a calibrated microphone 508 is electrically connected to the hearing aid input via pre-amp 510, thus bypassing the feedback path and the hearing aid microphone. The signal is recorded at 512.

A maximal-length sequence can be used as the excitation, and the impulse response of receiver 406 determined from the output of the calibrated external microphone connected to the audio input of the hearing aid. Or, as in the case of the feedback path estimation shown in FIG. 4, a white noise excitation can be used and a set of filter coefficients adapted to produce a model of the receiver response.

If only the magnitude frequency response is desired, the system can be excited with a sine-wave sweep and the response recorded at the hearing aid input, or individual tones can be used with the magnitude at each frequency determined at the hearing aid input. Distortion can be estimated by increasing the level of the sinusoids and measuring the power at the frequencies of the harmonics, or a noise signal can be used to measure the coherence between the excitation signal and the signal recorded at the hearing aid input.

The minimum digital signal level that drives the amplifier or receiver into saturation can be determined by increasing the level of a sinusoid excitation and observing the maximum output signal level. The maximum receiver output signal level for the D/A converter input at full scale can be determined by generating a sinusoid at full scale and measuring the output signal power.

FIG. 6 is a block diagram showing a third configuration for performing the measurement steps 206 and 306 of FIGS. 2 and 3.

The system shown in FIG. 6 can be used to estimate the characteristics of microphone 410 once the receiver impulse response or transfer function has been measured. Receiver 406 is connected directly to microphone 410 via a short acoustic tube 608, so the feedback path is bypassed but amplifier 404, receiver 406, and microphone 410 are included. Since the amplifier-receiver characteristics are already known, only the microphone remains to be measured. A maximal-length sequence, white noise, or a sinusoidal sweep or a set of tones can be used to measure the overall system response, after which the known receiver characteristics are divided out to produce the estimate of the microphone response.

There are several ways in which the measurements can be used to adjust the processing parameters. In a feedback cancellation system, for example, the impulse response of the feedback path can be used as the input to a system identification procedure to produce a nonvarying all-pole, all-zero, or pole-zero filter to model the feedback path or to provide the starting filter coefficients for an adaptive all-zero or pole-zero model. Receiver measurements made in an acoustic coupler can be used on the production line to check that the receiver sensitivity, maximum output signal level, frequency response, and distortion are within specifications. Differences in frequency response could then be used, for example, to adjust equalization used to compensate for irregularities in the receiver frequency response. An external microphone connected to a probe tube inserted in the ear canal along with the hearing aid earmold could be used to provide equalization for the receiver as it will be used in situ. The microphone response measurements can be used to provide equalization for the microphone in a manner similar to that used for the receiver. The receiver and microphone response and calibration curves can also be used to adjust compression parameters for each hearing aid so that the amplified input signal never exceeds the maximum digital level that can be handled by the DAC without distortion.

While the exemplary preferred embodiments of the present invention are described herein with particularity, those skilled in the art will appreciate various changes, additions, and applications other than those specifically mentioned, which are within the spirit of this invention.

What is claimed is:

1. Testing and initialization apparatus for a hearing aid, the hearing aid having a programmable digital signal processor capable of being programmed with a hearing aid processing program, the apparatus comprising:
    means for loading a testing program into the hearing aid digital signal processor memory;
    means built into the hearing aid and responsive to the testing program for providing a test signal;
    means built into the hearing aid and responsive to the testing program for recording the response of the hearing aid in the presence of the test signal;
    means for measuring hearing aid performance based on the recorded response;
    means for computing hearing aid parameters based upon the measured hearing aid performance; and
    means for loading a run time hearing aid processing program based upon the parameters into the digital signal processor memory.

2. The apparatus of claim 1, further comprising:
    storage memory in the hearing aid; and
    means for storing the testing program in the storage memory.

3. The apparatus of claim 2, wherein the means for measuring and the means for computing are built into the hearing aid.

4. The apparatus of claim 1, further comprising a host computer connected to the hearing aid, wherein the testing program is stored on the host computer prior to being loaded into the DSP.

5. The apparatus of claim 4 wherein the means for measuring and the means for computing reside on the host computer.

6. The apparatus of claim 1, wherein the means for recording comprises:
    means for introducing the test signal at the output of the hearing aid; and
    means for recording the resulting signal at the input of the hearing aid.

7. A hearing aid comprising:
    a hearing aid microphone for converting sound into an audio signal;
    a programmable digital signal processor (DSP) hearing aid processor, for processing the audio signal;
    a speaker, connected to the output of the hearing aid processor, for converting the processed audio signal; into a sound signal; and
    self testing and initialization apparatus including
        means for loading a testing program into the hearing aid DSP memory;
        means responsive to the testing program for providing a test signal;
        means responsive to the testing program for recording the response of the hearing aid in the presence of the test signal;
        means responsive to the testing program for measuring hearing aid performance based on the recorded response;
        means responsive to the testing program for computing hearing aid parameters based upon the measured hearing aid performance; and
        means for loading a run time hearing aid processing program based upon the performance parameters into the digital signal processor.

8. The hearing aid of claim 7, wherein the means for recording comprises:
    means for introducing the test signal prior to the speaker; and
    means for recording the resulting audio signal at the output of the hearing aid microphone.

9. The hearing aid of claim 7, wherein the means for recording the response comprises:
    means for introducing the test signal prior to the speaker;
    a test microphone for measuring the resulting audio signal at the output of the speaker; and
    means for recording the audio signal measured by the test microphone.

10. The hearing aid of claim 7, wherein the means for recording the response comprises:
    means for introducing the test signal prior to the speaker;
    an acoustic tube between the output of the speaker and the hearing aid microphone; and
    means for recording the audio signal at the output of the hearing aid microphone.

11. Self testing and initialization apparatus for a hearing aid, the hearing aid having a hearing aid microphone for converting sound into an audio signal, a programmable digital signal processor (DSP) having a memory and capable of being programmed with a hearing aid processing program for processing the audio signal, and a speaker, connected to the output of the DSP, for converting the processed audio signal into a sound signal, the self testing apparatus comprising:
    a host computer connected to the hearing aid;
    means for loading a testing program from the host computer into the DSP memory;
    means built into the hearing aid and responsive to the testing program for providing a test signal;
    means built into the hearing aid and responsive to the testing program for recording the response of the hearing aid in the presence of the test signal;

means in the host computer for measuring hearing aid performance based upon the recorded response;

means for in the host computer for computing hearing aid parameters based upon the measured hearing aid performance; and means for loading a run time hearing aid processing program based upon the performance parameters from the host computer into the DSP memory.

12. The apparatus of claim 11, wherein the means for recording the response comprises:

means for introducing the test signal prior to the speaker; and means for recording the resulting audio signal at the output of the hearing aid microphone.

13. The apparatus of claim 11, wherein the means for recording the response comprises:

means for introducing the test signal prior to the speaker;

a test microphone for measuring the resulting audio signal at the output of the speaker; and means for recording the audio signal measured by the test microphone.

14. The apparatus of claim 11, wherein the means for recording the response comprises:

means for introducing the test signal prior to the speaker;

an acoustic tube between the output of the speaker and the hearing aid microphone; and means for recording the audio signal at the output of the hearing aid microphone.

15. A method for testing and initializing a hearing aid, the hearing aid having a programmable digital signal processor (DSP) capable of being programmed with a hearing aid processing program, the method comprising the steps of:

loading a test program into the DSP memory;

producing a test signal;

recording the response of the hearing aid in the presence of the test signal;

measuring the performance of the hearing aid based upon the recorded response;

computing parameters based upon the measured performance; and loading a run time hearing aid processing program based upon the parameters into the DSP memory.

16. The method of claim 15, wherein the step of loading a test program downloads the test program from a host computer into the DSP.

17. The method of claim 16, wherein the measuring and computing steps are performed on the host computer.

18. The method of claim 16, wherein the measuring and computing steps are performed by the DSP.

19. The method of claim 15, wherein the step of loading the test program loads the test program from hearing aid storage memory.

* * * * *